United States Patent
Forester et al.

(10) Patent No.: US 6,242,618 B1
(45) Date of Patent: Jun. 5, 2001

(54) $H_2S$ SCAVENGERS FOR POLYSULFIDE PRODUCTS AND METHODS FOR SCAVENGING $H_2S$ FROM POLYSULFIDE PRODUCTS

(75) Inventors: David R. Forester, Concord; Bharat B. Malik, Euclid, both of OH (US)

(73) Assignee: The Lubrizol Corporation, Wickliffe, OH (US)

( * ) Notice: Subject to any disclaimer, the term of this patent is extended or adjusted under 35 U.S.C. 154(b) by 0 days.

(21) Appl. No.: 09/532,530

(22) Filed: Mar. 21, 2000

(51) Int. Cl.$^7$ .................. C07D 303/22; C07D 303/23
(52) U.S. Cl. ................. 549/555; 549/560; 208/237; 208/240
(58) Field of Search .................. 549/555, 560; 208/237, 240

(56) References Cited

U.S. PATENT DOCUMENTS

| | | | |
|---|---|---|---|
| 4,307,225 | 12/1981 | Louthan | 528/279 |
| 4,433,134 | 2/1984 | Louthan | 528/279 |
| 4,615,818 | 10/1986 | DeBiase et al. | 252/47.5 |
| 4,778,609 | 10/1988 | Koch et al. | 252/32.5 |
| 4,876,389 | 10/1989 | Gongors et al. | 568/26 |
| 4,978,512 | 12/1990 | Dillon | 423/226 |
| 5,008,432 | 4/1991 | Roberts | 558/436 |
| 5,074,991 | 12/1991 | Weers | 208/236 |
| 5,155,275 | 10/1992 | Shaw | 568/21 |
| 5,169,411 | 12/1992 | Weers | 44/421 |
| 5,206,439 | 4/1993 | Shaw | 568/21 |
| 5,218,147 | 6/1993 | Shaw | 568/21 |
| 5,223,127 | 6/1993 | Weers et al. | 208/236 |
| 5,266,185 | 11/1993 | Weers et al. | 208/47 |
| 5,284,576 | 2/1994 | Weers et al. | 208/236 |
| 5,344,971 | 9/1994 | Dedieu et al. | 562/512 |
| 5,354,453 | 10/1994 | Bhatia | 208/236 |
| 5,403,961 | 4/1995 | Shaw | 568/21 |
| 5,462,721 | 10/1995 | Pounds et al. | 423/226 |
| 5,539,060 | * 7/1996 | Tsunogae et al. | 525/338 |
| 5,552,060 | 9/1996 | Roof | 210/749 |
| 5,567,212 | 10/1996 | Gentry et al. | 44/420 |
| 5,674,377 | 10/1997 | Sullivan et al. | 208/208 |
| 5,688,478 | 11/1997 | Pounds et al. | 423/228 |
| 5,696,282 | 12/1997 | Shaw et al. | 560/152 |
| 5,744,024 | 4/1998 | Sullivan et al. | 208/236 |
| 5,773,482 | * 6/1998 | Ueno et al. | 521/99 |
| 6,069,211 | * 5/2000 | Reyes, Jr. et al. | 525/523 |

* cited by examiner

*Primary Examiner*—Ba K. Trinh
(74) *Attorney, Agent, or Firm*—Teresan W. Gilbert; Michael F. Esposito

(57) ABSTRACT

Invention relates to $H_2S$ scavengers polysulfide compounds and methods for scavenging $H_2S$ from polysulfide compounds. Furthermore, the invention uses a scavenger for selectively reducing the levels of hydrogen sulfide present in a polysulfide product.

11 Claims, No Drawings

H₂S SCAVENGERS FOR POLYSULFIDE PRODUCTS AND METHODS FOR SCAVENGING H₂S FROM POLYSULFIDE PRODUCTS

FIELD OF THE INVENTION

The present invention relates to $H_2S$ scavengers for polysulfide compounds and methods for scavenging $H_2S$ from polysulfide compounds. More particularly, the invention relates to use of a scavenger and methods for selectively reducing the levels of hydrogen sulfide present in a polysulfide product.

BACKGROUND OF THE INVENTION

Polysulfides have been found useful for many purposes, such as additives or elastomers, as antioxidants for lubricating oils, and useful in the compounding of extreme pressure lubricants.

Also, polysulfides provide a relatively high sulfur content source for presulfiding of metals on hydrotreating and hydrocracking catalysts that are used in various hydrogen refining processes, as well as distillate fuel and lube oil refining catalysts. Further, polysulfides are used as a sulfur passivation agent of heated metal surfaces in furnaces and separation processes related to hydrocarbon/steam pyrolysis processes to produce olefins and diolefins.

A conventional process for producing a polysulfide compound is to react a mercaptan, such as t-dodecylmercaptan, with elemental sulfur, in the presence of a catalyst. However, the resultant polysulfide contains unreacted mercaptans and residual $H_2S$.

Another example of the production of a polysulfide product is the reaction product of isobutylene, sulfur, and $H_2S$, with n-butyl amine used as a catalyst. A polysulfide containing about 54 wt % sulfur is the resultant product. Such a polysulfide product has been utilized as a catalyst presulfiding agent. Upon standing, this product generates $H_2S$ which evolves into the vapor space, in an amount up to 2000 ppm $H_2S$, as measured using the draeger tube method, or up to 50–60 ppm, as measured by the HS3-BM method, or up to about 30–50 ppm, when analyzed by the GC-headspace method. Because such a product has been sold as a low-odor alternative to dimethyl disulfide or dimethyl sulfide, any generation of $H_2S$ is undesirable by the industry. Due to the presence of $H_2S$, such a polysulfide has been formulated with 0.4 wt % of Tolad SX9200 (known as HSS-2, available from Baker Petrolite). Although HSS-2 works very well, it contains about 5 wt % nitrogen, which adds about 200 ppm of nitrogen to the resultant product. Also, it is suspected that the nitrogen based $H_2S$ scavenger can contribute to compatibility problems of the resultant formulation if water contamination is encountered.

The presence of $H_2S$ also contributes to an unpleasant odor, and presents many environmental and safety hazards. Hydrogen sulfide is highly flammable, toxic when inhaled, and strongly irritates the eyes and other mucous membranes.

Treatments to reduce or remove $H_2S$ have often been called "sweetening" treatments. The agent that is used to remove or reduce $H_2S$ levels sometimes is called a "scavenging" agent. The sweetening or scavenging of $H_2S$ from petroleum or natural gas is an example of where $H_2S$ level reduction or removal has been performed. Many aqueous substrates also have been treated to reduce or remove $H_2S$.

Attempts also have been made to remove unreacted mercaptans and residual $H_2S$ from a polysulfide product. For example, European Patent Application 0 076 376, published on Apr. 13, 1983, discloses that a newly synthesized polysulfide can be deodorized by treating the crude polysulfide with a metal salt of an inorganic or organic acid at an elevated temperature. However, the process requires a lengthy treatment to obtain a satisfactory result, and use of powdered anhydrous salt is preferred, which is more costly.

It is therefore very desirable to reduce the sulfur content of a polysulfide product utilizing a more attractive scavenger agent and method.

It is therefore one objective of the present invention to develop a process to stabilize a polysulfide compound so the subsequent release and/or generation of $H_2S$ is minimized and the desirable low odor properties of the polysulfide product(s) is maintained for extended periods of time. This is done by reducing unreacted or residual sulfur-containing compounds contaminating the polysulfide.

In addition, the use of an non-nitrogen containing $H_2S$ scavenger has the added benefit of lowering the amount of nitrogen added to the polysulfide, and subsequently to the catalyst or steam pyrolysis processes.

These objectives are accomplished with the present invention without adversely impacting the desirable properties of the polysulfide as a catalyst presulfiding or metal passivation agent.

Other advantages and features will become more apparent as the invention is more fully disclosed in the following disclosure and claims.

SUMMARY OF THE INVENTION

According to the present invention, a process for stabilizing and deodorizing a polysulfide product is provided which comprises contacting a polysulfide compound with a glycidyl ether compound. According to the present invention, glycidyl ethers have been found to significantly reduce $H_2S$ formation in a polysulfide product under storage conditions up to three months. Since these products do not contain nitrogen, they are more favorable as $H_2S$ scavengers for a formulated polysulfide product than HSS-2.

DETAILED DESCRIPTION OF THE PREFERRED EMBODIMENTS

The polysulfide compounds are those known in the art, as set forth, for example, in U.S. Pat. No. 5,696,282, U.S. Pat. No. 4,876,389, U.S. Pat. No. 5,155,275, U.S. Pat. No. 5,206,439, U.S. Pat. No. 5,403,961, and U.S. Pat. No. 5,218,147. These patents are incorporated herein in their entirety for the production of polysulfides.

A polysulfide can be described in general as a compound containing at least three sulfurs bonded in sequence, with the end sulfurs additionally bonded to a hydrocarbon group containing at least three carbons. A polysulfide useful in the present invention is the reaction product of isobutylene, sulfur, and $H_2S$, with n-butyl amine as a catalyst, exhibiting the following general polysulfide distribution, with S3 representing three sulfur atoms bonded to each other in sequence, S4 representing four sulfur atoms bonded to each other in sequence, and so on: 20–25 wt % S3, 25–30 wt % S4, 18–22 wt % S5, 10–14 wt % S6, 5–7 wt % S7, and 2–5 wt % S8 or higher (meaning 8 or more sulfur atoms bonded to each other in sequence).

The scavenging agents of the present invention are useful for treating polysulfide products containing $H_2S$.

More specifically, the scavenging agents of the present invention are glycidyl ether compounds having the following general formula:

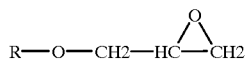

wherein R is C2–12 alkyl or allyl or phenyl.

Glycidyl ethers suitable for the present invention are glycidyl ether compounds selected from the group consisting of allyl glycidyl ether, isopropyl glycidyl ether, tert-butyl glycidyl ether, phenyl glycidyl ether, and ethylhexyl glycidyl ether. Tert-butyl or ethylhexyl glycidyl ether is preferred due to their lower volatility and toxicity, with ethylhexyl glycidyl ether being most preferred.

Commercially available products for each of these glycidyl ether compounds are allyl glycidyl ether available from Richman Chemical (AGEt), or from Raschig (AGE), and isopropyl glycidyl ether, tert-butyl glycidyl ether, ethyl hexyl glycidyl ether, or phenyl glycidyl ether, each available from Raschig. A specific commercially available product at Raschig is GE-100. GE-100 is described by Raschig as a mixture of di- and trifunctional epoxide polymers based on glycidyl glycerin ether. However, GE-100 has 12 wt % chlorine content which makes it less desirable for commercial applications.

According to the present invention, the polysulfide compound is contacted with from about 0.05 to about 1.0 wt %, preferably from about 0.2 to about 0.6 wt % of the glycidyl ether compound based upon the total weight of the mixture. The glycidyl ether compound is preferably mixed with the polysulfide compound at a temperature between 100° F. and 160° F., but can be added at any temperature suitable for mixing. The polysulfide is contacted with the scavenging agent for at least about 1 hour, at the desired mixing temperature.

The resultant product generates essentially no $H_2S$ upon standing when analyzed by any of the three methods mentioned above (draeger tube or HS3-BM, or GC-headspace methods). More particularly, when from 0.4 to 0.9 wt % AGEt, AGE, GE-100, or EHGE (ethylhexyl glycidyl ether) is added to a polysulfide product, then stored for one to three months at temperatures up to 140° F., the $H_2S$ generated is greatly reduced compared to the untreated polysulfide product.

Several glycidyl ethers were evaluated according to the present invention, and are exemplified below.

EXAMPLE 1

0.5 or 0.9 wt % of glycidyl ether polymer (GE-100 from Raschig) or allyl glycidyl ether (AGE from Raschig) was added to a polysulfide, and mixed well at room temperature, then stored at room temperature and at 140° F.

After 10 days storage at room temperature, GC headspace analyses (Table 1) showed GE-100 to be most effective at reducing $H_2S$ in the vapor space with almost complete reduction at a dosage of 0.9 wt %.

After storage at 140° F., both the GE-100 and the AGE were completely effective in reducing $H_2S$.

After one month storage at room temperature and at 140° F., GE-100 at 0.5 wt % was completely effective in reducing $H_2S$ in the vapor space, while 0.9 wt % AGE was required for similar efficacy (Table 1).

After storage at 140° F., both compounds at 0.5 wt % showed almost complete effectiveness in reducing $H_2S$.

TABLE 1

| Item | Wt % of scavenging agent mixed with polysulfide product | Amount of $H_2S$ at room Temperature (10 days) | Amount of $H_2S$ at 120° F. (10 days) | Amount of $H_2S$ at room Temperature (31 days) | Amount of $H_2S$ at 120° F. (31 days) |
|---|---|---|---|---|---|
| Polysulfide Product* | 0.0 | 34 | 34 | 33 | 28 |
| GE 100** | 0.5 | 19.2 | <0.1 | <0.1 | <0.1 |
| GE 100** | 0.9 | 0.11 | <0.1 | 0.23 | <0.1 |
| AGE*** | 0.5 | 28.5 | 0.14 | 5.0 | 0.2 |
| AGE*** | 0.9 | 19.4 | <0.1 | 1.6 | 0.8 |

*A reaction product of isobutylene, sulfur and $H_2S$ with n-butyl amine catalyst
**GE 100 is a glycidyl ether polymer available at Raschig
***AGE available at Raschig.

Since the GE-100 contains about 12 wt % chlorine content, alternate glycidyl ethers from both Raschig and Richmond Chemical were evaluated, and are discussed in Example 2, below.

EXAMPLE 2

Treatment of the polysulfide product with 0.4% or 0.8 wt % phenyl or ethylhexyl glycidyl ether (PGE or EGE from Raschig) and 0.4 or 0.8% allyl glycidyl ether (AGEt from Richmond Chemical) were compared to similar dosages of HSS-2. All of these blends were stored for 12, 30 or 90 days at room temperature or 140° F.

Using GC headspace analyses, the 12-day data (Table 2) showed the 0.8 wt % AGEt or 0.4 wt % HSS-2 to be completely effective in reducing $H_2S$ at either storage temperature. After storage at 140° F. for 12 days, 0.4 wt % of AGEt or 0.8 wt % PGE were almost as effective as 0.4 wt % HSS-2.

All of these compounds showed significant $H_2S$ reduction after one month storage at either temperature, and all except PGE stored at room temperature were essentially equivalent to 0.4 wt % HSS-2.

GC headspace results after 90 days storage further confirmed the generally equivalent efficacy of all these compounds at 0.4 wt % in reducing $H_2S$ in the polysulfide product (Table (2).

All of these treated polysulfides were compared to the untreated polysulfide in the HS3-M test after 30 days storage at room temperature. In the HS3B-M test, the polysulfide is purged with nitrogen for 24 hours. The purged gases are collected in a gas sampling bag, then analyzed for $H_2S$ by GC. The result is a weighted average $H_2S$ concentration over the 24 hour purge period. The results are shown in Table 3. As shown in Table 3, all of the glycidyl treated polysulfides resulted in significantly lower levels of $H_2S$ than the untreated polysulfide.

TABLE 2

| Sample No. | Item | Wt % of scavenging agent mixed with polysulfide product | Amount of H₂S at room temperature (12 days) | Amount of H₂S at 140° F. (12 days) | Amount of H₂S at room temperature (30 days) | Amount of H₂S at 140° F. (30 days) | Amount of H₂S at 140° F. (90 days) | Amount of H₂S at 140° F. (90 days) |
|---|---|---|---|---|---|---|---|---|
| 1 | Polysulfide Product* | 0.0 | 34 | 38 | 60 | 29 | 38 | 1.2 |
| 2 | PGE** | 0.4 | 13 | 2.9 | 11 | <0.1 | 0.6 | 0.2 |
| 3 | PGE** | 0.8 | 7.4 | 0.4 | 1.9 | <0.1 | <0.1 | <0.1 |
| 4 | EHGE*** | 0.4 | 5.2 | 1.4 | 0.1 | <0.1 | <0.1 | <0.1 |
| 5 | EHGE*** | 0.8 | 8.3 | 5.8 | <0.1 | <0.1 | <0.1 | <0.1 |
| 6 | AGEt**** | 0.4 | 3.8 | 0.5 | 0.4 | <0.1 | <0.1 | <0.1 |
| 7 | AGEt**** | 0.8 | 0.2 | <0.1 | <0.1 | <0.1 | <0.1 | <0.1 |
| 8 | HSS-2***** | 0.4 | 0.1 | <0.1 | <0.1 | <0.1 | <0.1 | <0.1 |
| 9 | HSS-2***** | 0.8 | <0.1 | <0.1 | <0.1 | 0.2 | <0.1 | <0.1 |

*Polysulfide product is a reaction product of isobutylene, sulfur and H2S with n-butyl amine catalyst
**The phenyl glycidyl ether is available from Raschig
***The ethyl hexyl glycidyl ether is available from Raschig
****The allyl glycidyl ether is available from Richman Chemical
*****HSS-2 is Tolad SX-9200 is available from Baker Petrolite

TABLE 3

| Sample No. | Item | Wt % of scavenging agent mixed with polysulfide Product | HS3B_M Test Data after 30 days storage at RT - H₂S, ppm |
|---|---|---|---|
| 1 | Polysulfide Product* | 0.0 | 45 |
| 2 | PGE** | 0.4 | 5 |
| 3 | PGE** | 0.8 | 0 |
| 4 | EHGE*** | 0.4 | 1 |
| 5 | EHGE*** | 0.8 | 2 |
| 6 | AGEt**** | 0.4 | 0 |
| 7 | AGEt**** | 0.8 | 0 |
| 8 | HSS-2***** | 0.4 | 0 |
| 9 | HSS-2***** | 0.8 | 0 |

*Polysulfide product is a reaction product of isobutylene, sulfur and H₂S with n-butyl amine catalyst
**The phenyl glycidyl ether is available from Raschig
***The ethyl hexyl glycidyl ether is available from Raschig
****The allyl glycidyl ether is available from Richman Chemical
*****HSS-2 is Tolad SX-9200 is available from Baker Petrolite It should be understood that the forms of the invention described herein are exemplary only and are not intended as limitations on the scope of the present invention as defined in the appended claims.

What is claimed is:

1. A method of treating a polysulfide comprising, contacting said polysulfide with a glycidyl ether compound.

2. The method of claim 1, wherein said glycidyl ether compound is used in an amount of from about 0.05 to about 1.0 wt %, based upon the combined weight of said polysulfide and said glycidyl ether compound.

3. The method of claim 1, wherein said glycidyl ether compound is used in an amount of from about 0.2 to about 0.6 wt %, based upon the combined weight of said polysulfide and said glycidyl ether compound.

4. The method of claim 1, wherein said glycidyl ether compound is combined with said polysulfide at a temperature suitable for mixing.

5. The method of claim 1, wherein said glycidyl ether compound is combined with said polysulfide at a temperature between about 100° F. and about 160° F.

6. The method of claim 1, wherein said polysulfide is contacted with said glycidyl ether compound for at least about one hour, at the desired mixing temperature.

7. The method of claim 1, wherein said glycidyl ether compound has the following general formula:

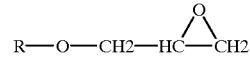

wherein R is C2–12 alkyl or allyl or phenyl.

8. The method of claim 1, wherein said polysulfide is a compound containing at least three sulfurs bonded in sequence, with end sulfurs additionally bonded to a hydrocarbon group containing at least three carbons.

9. The method of claim 1, wherein said polysulfide is the reaction product of isobutylene, sulfur, and H₂S, with n-butyl amine as a catalyst.

10. The method of claim 1, wherein said polysulfide has the following general polysulfide distribution: 20–25 wt % S3, 25–30 wt % S4, 18–22 wt % S5, 10–14 wt % S6, 5–7 wt % S7, and 2–5 wt % S8 or more.

11. The method of claim 1, wherein said glycidyl ether compound is selected form the group consisting of allyl glycidyl ether, isopropyl glycidyl ether, tert-butyl glycidyl ether, phenyl glycidyl ether, and ethylhexyl glycidyl ether.

* * * * *